US008748460B2

(12) United States Patent
Ramstedt et al.

(10) Patent No.: US 8,748,460 B2
(45) Date of Patent: Jun. 10, 2014

(54) IMINOSUGARS AND METHODS OF TREATING TOGAVIRAL DISEASES

(71) Applicants: United Therapeutics Corporation, Silver Spring, MD (US); The Chancellor, Masters and Scholars of the University of Oxford, Oxford (GB)

(72) Inventors: Urban Ramstedt, Bethesda, MD (US); Brennan Klose, Washington, DC (US); Nicole Zitzmann, Oxford (GB); Raymond A. Dwek, Oxford (GB); Terry D. Butters, Oxford (GB)

(73) Assignees: United Therapeutics Corporation, Silver Spring, MD (US); The Chancellor, Masters and Scholars of the University of Oxford, Oxford (GB)

( * ) Notice: Subject to any disclaimer, the term of this patent is extended or adjusted under 35 U.S.C. 154(b) by 0 days.

(21) Appl. No.: 13/761,583

(22) Filed: Feb. 7, 2013

(65) Prior Publication Data

US 2013/0150405 A1    Jun. 13, 2013

Related U.S. Application Data

(63) Continuation of application No. 12/813,882, filed on Jun. 11, 2010, now Pat. No. 8,426,445.

(60) Provisional application No. 61/186,614, filed on Jun. 12, 2009.

(51) Int. Cl.
*A61K 31/445* (2006.01)

(52) U.S. Cl.
USPC ........................................................ 514/328

(58) Field of Classification Search
USPC ........................................................ 514/328
See application file for complete search history.

(56) References Cited

U.S. PATENT DOCUMENTS

| | | | |
|---|---|---|---|
| 4,182,767 A | 1/1980 | Murai et al. |
| 4,246,345 A | 1/1981 | Kinast et al. |
| 4,260,622 A | 4/1981 | Junge et al. |
| 4,266,025 A | 5/1981 | Kinast et al. |
| 4,278,683 A | 7/1981 | Stoltefuss et al. |
| 4,405,714 A | 9/1983 | Kinast et al. |
| 4,639,436 A | 1/1987 | Junge et al. |
| 4,806,650 A | 2/1989 | Schroeder et al. |
| 4,994,572 A | 2/1991 | Fleet |
| 5,030,638 A | 7/1991 | Partis et al. |
| 5,043,273 A | 8/1991 | Scudder et al. |
| 5,103,008 A | 4/1992 | Scudder et al. |
| 5,200,523 A | 4/1993 | Fleet |
| 5,472,969 A | 12/1995 | Platt et al. |
| 5,550,243 A | 8/1996 | Khanna et al. |
| 5,622,972 A | 4/1997 | Bryant et al. |
| 6,465,487 B1 | 10/2002 | Block et al. |
| 6,495,570 B2 | 12/2002 | Jacob et al. |
| 6,545,021 B1 | 4/2003 | Mueller et al. |
| 6,610,703 B1 | 8/2003 | Jacob et al. |
| 6,689,759 B1 | 2/2004 | Jacob et al. |
| 6,696,059 B2 | 2/2004 | Jacob et al. |
| 6,809,803 B1 | 10/2004 | O'Brien et al. |
| 7,256,005 B2 | 8/2007 | Zitzmann et al. |
| 7,446,098 B2 | 11/2008 | Fan |
| 7,799,782 B2 | 9/2010 | Munson et al. |
| 8,426,445 B2 * | 4/2013 | Ramstedt et al. ............. 514/328 |
| 2004/0110795 A1 | 6/2004 | Zitzmann et al. |
| 2005/0256168 A1 | 11/2005 | Block et al. |
| 2006/0074107 A1 | 4/2006 | Butters et al. |
| 2006/0153829 A1 | 7/2006 | Fan |
| 2006/0251680 A1 | 11/2006 | Dwek et al. |
| 2006/0264467 A1 | 11/2006 | Mugrage et al. |
| 2007/0178081 A1 | 8/2007 | Fan |
| 2007/0244184 A1 | 10/2007 | Pinto et al. |
| 2007/0275998 A1 | 11/2007 | Butters et al. |
| 2008/0131398 A1 | 6/2008 | Jeffs et al. |
| 2008/0138351 A1 | 6/2008 | Dwek et al. |
| 2009/0186847 A1 | 7/2009 | Stein et al. |
| 2009/0186862 A1 | 7/2009 | Aerts et al. |
| 2009/0252785 A1 | 10/2009 | Pollock et al. |
| 2010/0004156 A1 | 1/2010 | Kaushal et al. |
| 2010/0068141 A1 | 3/2010 | Kaushal et al. |
| 2011/0189771 A1 | 8/2011 | Block et al. |

FOREIGN PATENT DOCUMENTS

| | | |
|---|---|---|
| EP | 1 061 922 B1 | 12/2000 |
| EP | 1 137 416 B1 | 10/2001 |
| EP | 1 714 676 A2 | 10/2006 |
| WO | WO 00/33843 A1 | 6/2000 |
| WO | WO 01/07078 A1 | 2/2001 |
| WO | WO 2004/074450 A2 | 9/2004 |
| WO | WO 2006/077427 A2 | 7/2006 |
| WO | WO 2006/124676 A1 | 11/2006 |
| WO | WO 2007/014327 A2 | 2/2007 |
| WO | WO 2007/123403 A1 | 11/2007 |
| WO | WO 2008/068548 A1 | 6/2008 |
| WO | WO 2008/088581 A2 | 7/2008 |

OTHER PUBLICATIONS

U.S. Appl. No. 61/282,507, filed Feb. 22, 2010, Ramstedt et al.
U.S. Appl. No. 61/272,252, filed Sep. 4, 2009, Ramstedt et al.
U.S. Appl. No. 61/272,253, filed Sep. 4, 2009, Ramstedt et al.
U.S. Appl. No. 61/272,254, filed Sep. 4, 2009, Ramstedt et al.
U.S. Appl. No. 61/282,508, filed Feb. 22, 2010, Ramstedt et al.
U.S. Appl. No. 61/353,935, filed Jun. 11, 2010, Ramstedt et al.
U.S. Appl. No. 12/656,992, filed Feb. 22, 2010, Ramstedt et al.
U.S. Appl. No. 12/656,993, filed Feb. 22, 2010, Ramstedt et al.
U.S. Appl. No. 12/732,630, filed Mar. 26, 2010, Pollock et al.
U.S. Appl. No. 12/873,708, filed Sep. 1, 2010, Ramstedt et al.

(Continued)

*Primary Examiner* — Rei-tsang Shiao
(74) *Attorney, Agent, or Firm* — Foley & Lardner LLP (57) ABSTRACT

Provided are novel methods of treating and/or preventing a disease or condition caused by or associated with a virus belonging to the Togaviridae family using iminosugars, such as DNJ derivatives.

19 Claims, 9 Drawing Sheets

(56) References Cited

OTHER PUBLICATIONS

U.S. Appl. No. 12/873,704, filed Sep. 1, 2010, Ramstedt et al.
U.S. Appl. No. 12/873,705, filed Sep. 1, 2010, Ramstedt et al.
Ahmed et al., "Antiviral Activity and Metabolism of the Castanospermine Derivative MDL 28,574, In Cells Infected with Herpes Simplex Virus Type 2," Biochemical and Biophysical Research Communications, Mar. 8, 1995, 208(1):267-273.
Berge et al., "Pharmaceutical Salts," J. Pharm. Sci., Jan. 1977, 66(1):1-18.
Branza-Nichita et al., "Antiviral Effect of N-Butyldeoxynojirimycin against Bovine Viral Diarrhea Virus Correlates with Misfolding E2 Envelope Proteins and Impairment of their Association into E1-E2 Heterodimers," J. Virol., Apr. 2001, 75(8):3527-3536.
Bridges et al., "The effect oral treatment with 6-O-butanoyl castanospermine (MDL 28,574) in the murine zosteriform model of HSV-1 infection," Glycobiology, 1995, 5(2):249-253.
Butters et al., "Imino sugar inhibitors for treating the lysosomal glycosphingolipidoses," Glycobiology, 2005, 15(10):43R-52R.
Choukhi et al., Involvement of Endoplasmic Reticulum Chaperones in the Folding of Hepatitis C Virus Glycoproteins, (1998) J. Virol., 72(5), pp. 3851-8.
Courageot et al., "a-Glucosidase Inhibitors Reduce Dengue Virus Production by Affecting the Initial Steps of Virion Morphogenesis in the Endoplasmic Reticulum," (2000) J. Virol., 74(1): pp. 564-572.
Datema et al., "On the Role of Oligosaccharide Trimming in the Maturation of Sindbis and Influenza Virus," Archives of Virology, 1984, 81:25-39.
Dwek et al., "Targeting glycosylation as a therapeutic approach," Nature Reviews, Drug Discovery, Jan. 2002, 1:65-75.
Gretch et al., "Characterization of a Human Cytomegalovirus Glycoprotein Complex (gcI)," J. Gen. Virol., 1988, 69:1205-1215.
Hollinger et al., "Heptatis B Virus," Fields Virology, 2001, Fourth Ed., vol. 2, Chapter 87, 2971-3036.
Huang et al., "Antiviral activity of some natural and synthetic sugar analogues," FEBS Letters, 10257, Oct. 1991, 291(2):199-202.
Jarvis et al,. "Biosynthesis and Processing of the *Autographa califomica* Nuclear Polyhedrosis Virus gp64 Protein," Virology, 1994, 205:300-313.
Ka Uza et al., "The Significance of Carbohydrate Trimming for the Antigenicity of the Semlike Forest Virus Glycoprotein $E_2$," Virology, 1990, 176:369-378.
Lad et al., "Effect of Tunicamycin on Expression of Epitopes on Japanese Encephalitis Virus Glycoprotein E in Porcine Kidney Cells," Acta Virologica, 2000, 44:359-364.
Malvoisin et al., "The Role of N-Glycosylation in Cell Fusion Induced by a Vaccinia Recombinant Virus Expressing Both Measles Virus Glycoproteins," Virology, 1994, 200:11-20.

McDowell et al., "Glucose Trimming and Mannose Trimming Affect Different Phases of the Maturation of Sindbis Virus in Infected BHK Cells," Virology, 1987, 161:37-44.
Mehta et al., "Alpha-Galactosylceramide and Novel Synthetic Glycolipids Directly Induce the Innate Host Defense Pathway and Have Direct Activity Against Hepatitis B and C Viruses," Antimicrobial Agents and Chemotherapy, Jun. 2004, 48(6):2085-2090.
Mehta et al., "Imino sugars that are less toxic but more potent as antivirals, in vitro, compared with N-n-nonyl DNJ," Antiviral Chemistry & Chemotherapy, 2002, 13:299-304.
Nash et al., CAS: 145:180926, 2006, 5 pages/.
Ratner et al., "Inhibition of HIV and SIV Infectivity by Blockade of α-Glucosidase Activity," Virology, 1991, 181:180-192.
Repges-Illguth et al., "Differences in antigenicity of E2 in Semliki Forest virus particles and in infected cells," Arch. Virol., 1994, 135:433-435.
Repp et al., "The Effects of Processing Inhibitors of N-Linked Oligosaccharides on the Intracellular Migration of Glycoprotein E2 of Mouse Hepatitis Virus and the Maturation of Coronavirus Particles," J. Biol. Chem., Dec. 15, 1985, 260(29):15873-15879.
Schlesinger et al., "The Formation of Vesicular Stomatitis Virus (San Juan Strain) Becomes Temperature-sensitive When Glucose Residues Are Retained on the Oligosaccharides of the Glycoprotein," J. Biol. Chem., Jun. 25, 1984, 259(12):7597-7601.
Shresta et al., "Murine Model for Dengue Virus-Induced Lethal Disease with Increased Vascular Permeability," Journal of Virology, Oct. 2006, 80(20):10208-10217.
Silber et al., "The effects of oligosaccharide trimming inhibitors on glycoprotein expression and infectivity of Junin virus," FEMS Microbiology Letters, 1993, 109:39-44.
Sunkara et al., "Antiretroviral Activity of Castanospermine and Deoxynojirimycin, Specific Inhibitors of Glycoprotein Processing," Biochemical and Biophysical Research Communications, 1987, 148(1):206-210.
Taylor et al., "6,0-Butanoylcastanospermine (MDL 28,574) inhibits glycoprotein processing and the HIVs," AIDS, 1991, 5:693-698.
Taylor et al., "Loss of cytomegalovirus infectivity after treatment with castanospermine or related plant alkaloids correlates with aberrant glycoprotein synthesis," Antiviral Research, 1988, 10:11-26.
Wright et al., "Post-translational Processing of the Glycoproteins of Lymphocytic Choriomeningitis Virus," Virology, 1990, 177:175-183.
Zitzmann et al., "Imino sugars inhibit the formation and secretion of bovine viral diarrhea virus, a pestivirus model of hepatitis C virus: Implications for the development of broad spectrum anti-hepatitis virus agents," PNAS, Oct. 12, 1999, 96(21):11878-11882.

\* cited by examiner

| Compound | Activity vs. viral families IC50, uM | | | |
|---|---|---|---|---|
| | Bunya | Toga | | |
| | RVFV | VEEV | CHIKV | |
| NB-DNJ | 250 | 156 | >500 | |
| NN-DNJ | 58 | 12 | 56 | |
| N7-O-DNJ | 220 | >250 | 500 | |
| N9-DNJ | 250 | >250 | 500 | |
| NAP-DNJ | 49 | 2 | 22 | |

Virus abbreviations:
RVFV - Rift Valley fever
VEEV - Venezuelan equine encephalitis
CHIKV - Chikungunya

FIGURE 6

RVFV - Rift Valley fever virus

FIGURE 7

VEEV – Venezuelan equine encephalitis virus
Source: Unither Virology

FIGURE 8

IMINOSUGARS AND METHODS OF TREATING TOGAVIRAL DISEASES

CROSS-REFERENCE TO RELATED APPLICATIONS

This application is a Continuation of U.S. application Ser. No. 12/813,882, filed Jun. 11, 2010, which claims priority from U.S. Provisional Application No. 61/186,614, filed Jun. 12, 2009, the entire contents of which are incorporated herein by reference.

FIELD

The present application relates to iminosugars and methods of treating viral diseases with iminosugars and, in particular, to the use of iminosugars for treatment and prevention of diseases caused by or associated with a virus that belongs to the Bunyaviridae or Togaviridae family.

SUMMARY

One embodiment provides a method of treating or preventing a disease or condition caused by or associated with a virus belonging to the Bunyaviridae family, the method comprising administering to a subject in need thereof a compound of the formula, or a pharmaceutically acceptable salt thereof, wherein R is either selected from substituted or unsubstituted alkyl groups, substituted or unsubstituted cycloalkyl groups, substituted or unsubstituted aryl groups, or substituted or unsubstituted oxaalkyl groups; or wherein R is $R_1$ is a substituted or unsubstituted alkyl group;
$X_{1-5}$ are independently selected from H, $NO_2$, $N_3$, or $NH_2$;
Y is absent or is a substituted or unsubstituted $C_1$-alkyl group, other than carbonyl; and
Z is selected from a bond or NH; provided that when Z is a bond, Y is absent, and provided that when Z is NH, Y is a substituted or unsubstituted $C_1$-alkyl group, other than carbonyl; and wherein $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups.

Another embodiment provides a method of treating or preventing a disease or condition caused by or associated with a virus belonging to the Togaviridae family, the method comprising administering to a subject in need thereof a compound of the formula, or a pharmaceutically acceptable salt thereof, wherein R is either selected from substituted or unsubstituted alkyl groups, substituted or unsubstituted cycloalkyl groups, substituted or unsubstituted aryl groups, or substituted or unsubstituted oxaalkyl groups; or wherein R is $R_1$ is a substituted or unsubstituted alkyl group;
$X_{1-5}$ are independently selected from H, $NO_2$, $N_3$, or $NH_2$;
Y is absent or is a substituted or unsubstituted $C_1$-alkyl group, other than carbonyl; and
Z is selected from a bond or NH; provided that when Z is a bond, Y is absent, and provided that when Z is NH, Y is a substituted or unsubstituted $C_1$-alkyl group, other than carbonyl; and wherein $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups.

DRAWINGS

FIGS. 1(A)-(E) present chemical formulas of the following iminosugars: A) N-Butyl deoxynojirimycin (NB-DNJ or UV-1); B) N-Nonyl dexoynojirimycin (NN-DNJ or UV-2); C) N-(7-Oxadecyl)deoxynojirimycin (N7-O-DNJ or UV-3); D) N-(9-Methoxynonyl)deoxynojirimycin (N9-DNJ or UV-4); E) N—(N-{4'-azido-2'-nitrophenyl}-6-aminohexyl) deoxynojirimycin (NAP-DNJ or UV-5).

FIGS. 3A-D illustrate synthesis of N7-O-DNJ. In particular, FIG. 3C illustrates preparation of 6-propyloxy-1-hexanal; FIG. 3D illustrates synthesis of N7-O-DNJ.

FIGS. 4A-C relate to synthesis of N-(9-Methoxynonyl) deoxynojirimycin. In particular, FIG. 4C illustrates synthesis of N-(9-Methoxynonyl)deoxynojirimycin.

DETAILED DESCRIPTION

Definition of Terms

Unless otherwise specified, "a" or "an" means "one or more."

As used herein, the term "viral infection" describes a diseased state, in which a virus invades a healthy cell, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection.

As used herein, the term "treating or preventing viral infection" means to inhibit the replication of the particular virus, to inhibit viral transmission, or to prevent the virus from establishing itself in its host, and to ameliorate or alleviate the symptoms of the disease caused by the viral infection. The treatment is considered therapeutic if there is a reduction in viral load, decrease in mortality and/or morbidity.

IC50 or IC90 (inhibitory concentration 50 or 90) is a concentration of a therapeutic agent, such as an iminosugar, used to achieve 50% or 90% reduction of viral load, respectively.

DISCLOSURE

The present inventors discovered that certain iminosugars, such as deoxynojirimycin derivatives, can be effective against viruses that belong to the Bunyaviridae or Togaviridae family and, thus, these iminosugars can be useful for treating or preventing a disease or condition caused by or associated with a virus that belongs to the Bunyaviridae or Togaviridae family The family Bunyaviridae contains the following genera: Genus *Hantavirus*; Genus *Nairovirus*; Genus *Orthobunyavirus*; Genus *Phlebovirus*; Genus *Tospovirus*; Genus *Tenuivirus*. Of these genera, all can infect vertebrates except Tospoviruses, which can only infect arthropods and plants.

Genus *Hantavirus* includes the following viruses: Andes virus (ANDY); Bayou virus (BAYV); Black Creek Canal Virus (BCCV); Cano Delgadito virus (CADV); Choclo virus (CHOV); Dobrava-Belgrade virus (DOBV); Hantaan virus (HNTV); Isla Vista virus (ISLAV); Khabarovsk virus (KHAV); Laguna Negra virus (LANV); Muleshoe virus (MULV); New York virus (NYV); Prospect Hill Virus (PHV); Puumala virus (PMV); Rio Mamore virus (RIOMV); Rio Segundo virus (RIOSV); Seoul virus (SEOV); Sin Nombre virus (SNV); Thailand virus (THAIV); Thottapalayam (TPMV); Topografov virus (TOPV); Tula virus (TULV); Bakau virus.

Genus *Nairovirus* includes the following viruses: Crimean-Congo hemorrhagic fever virus; Dugbe Virus; Qalyub Virus; Sakhalin Virus; Dera Ghazi Khan; Thiafora Virus; and Hughes Virus.

Genus *Orthobunyavirus* includes La Crosse virus; California encephalitis virus and Jamestown Canyon virus.

Genus *Phlebovirus* includes Alenquer virus, Chandiru virus, Chagres virus, Sandfly Fever Naples virus, Sandfly Fever Sicilian virus, Sandfly Fever Toscana virus, Rift Valley Fever virus and Punta Toro virus.

Diseases and conditions that can be caused by or associated with viruses, that belong to the family Bunyaviridae, include, but not limited to, *Hantavirus* infection; hemorrhagic fever with renal syndrome (HFRS), which can be caused by a virus of *Hantavirus* Genus, such as Hantaan virus, Puumala virus, Seoul virus and Dobrava virus; *Hantavirus* cardiopulmonary syndrome (HCPS or HPS), which can be caused by a virus of *Hantavirus* Genus, such as Sin Nombre virus, Andes virus, New York virus, Bayou virus, and Black Creek Canal virus; Nephropathia epidemica, which can be caused by Puumala virus; hemorrhagic fever caused by Seoul virus; Sweating sickness; Crimean-Congo hemorrhagic fever; La Crosse encephalitis; California encephalitis, which can be caused by a virus of Genus *Orthobunyavirus*, such as La Crosse virus, California encephalitis virus and Jamestown Canyon virus; Phlebotomus fever; and Rift Valley fever.

The Togabiridae family includes Genus *Alphavirus* and Genus *Rubivirus*.

Genus *Alphavirus* includes the following viruses: Sindbis virus; Semliki Forest virus; O'nyong'nyong virus; Chikungunya virus; Mayaro virus; Ross River virus; Barmah Forest virus; Eastern equine encephalitis virus; Western equine encephalitis virus; and Venezuelan equine encephalitis virus. Genus *Rubivirus* includes Rubella viruses.

Diseases and conditions that can be caused by or associated with viruses, that belong to the family Togaviridae, include, but not limited to, sindbis fever; O'nyong'nyong fever; Chikungunya disease; Ross River fever; Barmah Forest virus infection; Eastern equine encephalitis; Western equine encephalitis; Venezuelan equine encephalitis and Rubella.

The iminosugar can be a compound of the following formula:

$$\begin{array}{c} W_2O \\ W_1O_{\prime\prime\prime\prime} \diagup\!\!\!\diagdown_{\prime\prime\prime\prime}OW_3 \\ \diagdown\!\!\!\diagup\!\!\!\diagdown\!\!\!\diagup CH_2OW_4 \\ N \\ | \\ R \end{array}$$

where $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups.

In some embodiments, R can be selected from substituted or unsubstituted alkyl groups, substituted or unsubstituted cycloalkyl groups, substituted or unsubstituted aryl groups, or substituted or unsubstituted oxaalkyl groups.

In some embodiments, R can be substituted or unsubstituted alkyl groups and/or substituted or unsubstituted oxaalkyl groups comprise from 1 to 16 carbon atoms, from 4 to 12 carbon atoms or from 8 to 10 carbon atoms. The term "oxaalkyl" refers to an alkyl derivative, which can contain from 1 to 5 or from 1 to 3 or from 1 to 2 oxygen atoms. The term "oxaalkyl" includes hydroxyterminated and methoxyterminated alkyl derivatives.

In some embodiments, R may be selected from, but is not limited to —$(CH_2)_6OCH_3$, —$(CH_2)_6OCH_2CH_3$, —$(CH_2)_6O(CH_2)_2CH_3$, —$(CH_2)_6O(CH_2)_3CH_3$, —$(CH_2)_2O(CH_2)_5CH_3$, —$(CH_2)_2O(CH_2)_6CH_3$, and —$(CH_2)_2O(CH_2)_7CH_3$.

In some embodiments, R may be an branched or unbranched, substituted or unsubstituted alkyl group. In certain embodiments, the alkyl group may be a long chain alkyl group, which may be C6-C20 alkyl group; C8-C16 alkyl group; or C8-C10 alkyl group.

In some embodiments, R can have the following formula where $R_1$ is a substituted or unsubstituted alkyl group;
$X_{1-5}$ are independently selected from H, $NO_2$, $N_3$, or $NH_2$;
Y is absent or is a substituted or unsubstituted $C_1$-alkyl group, other than carbonyl; and
Z is selected from a bond or NH; provided that when Z is a bond, Y is absent, and provided that when Z is NH, Y is a substituted or unsubstituted $C_1$-alkyl group, other than carbonyl.

In some embodiments, Z is NH and $R_1$—Y is a substituted or unsubstituted alkyl group, such as C2-C20 alkyl group or C4-C12 alkyl group or C4-C10 alkyl group.

In some embodiments, $X_1$ is $NO_2$ and $X_3$ is $N_3$. In some embodiments, each of $X_2$, $X_4$ and $X_5$ is hydrogen.

In some embodiments, the iminosugar is a DNJ derivative disclosed in U.S. Patent application publication no. 2007/0275998, which is incorporated herein by reference.

Figure 1A:
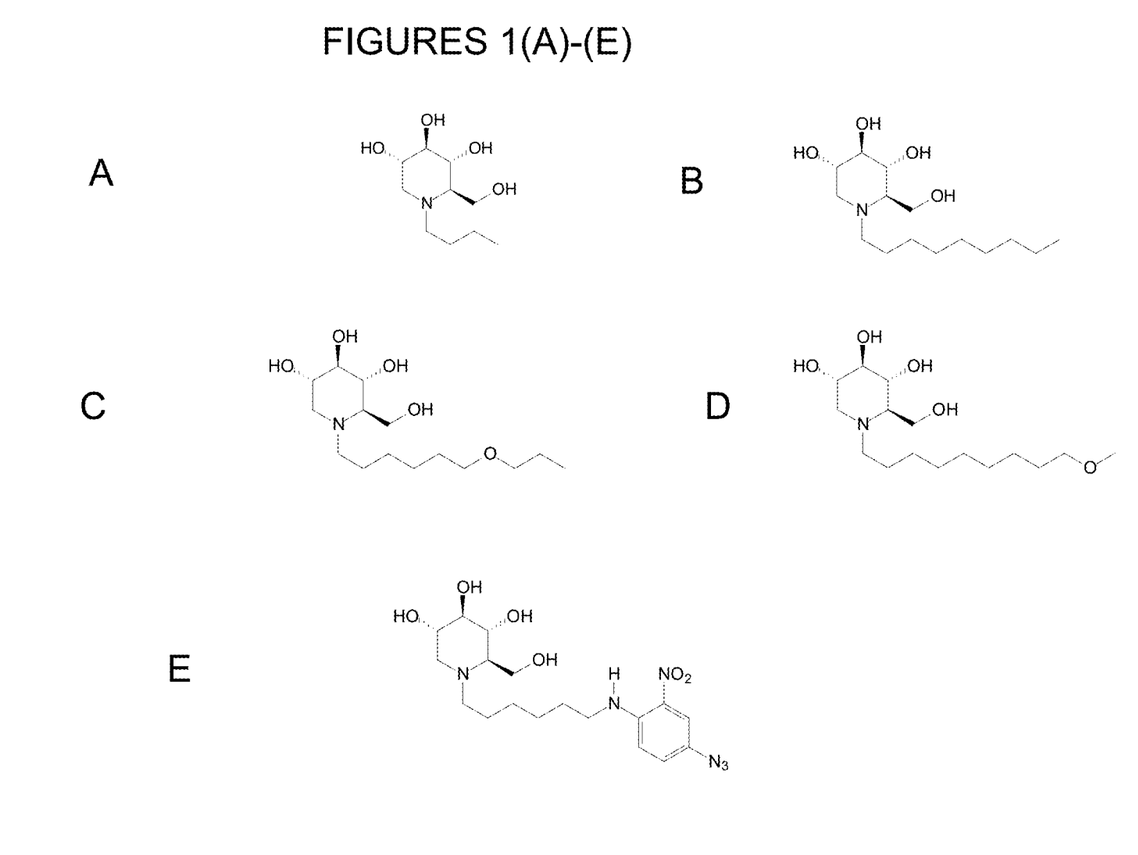
Figure 2:
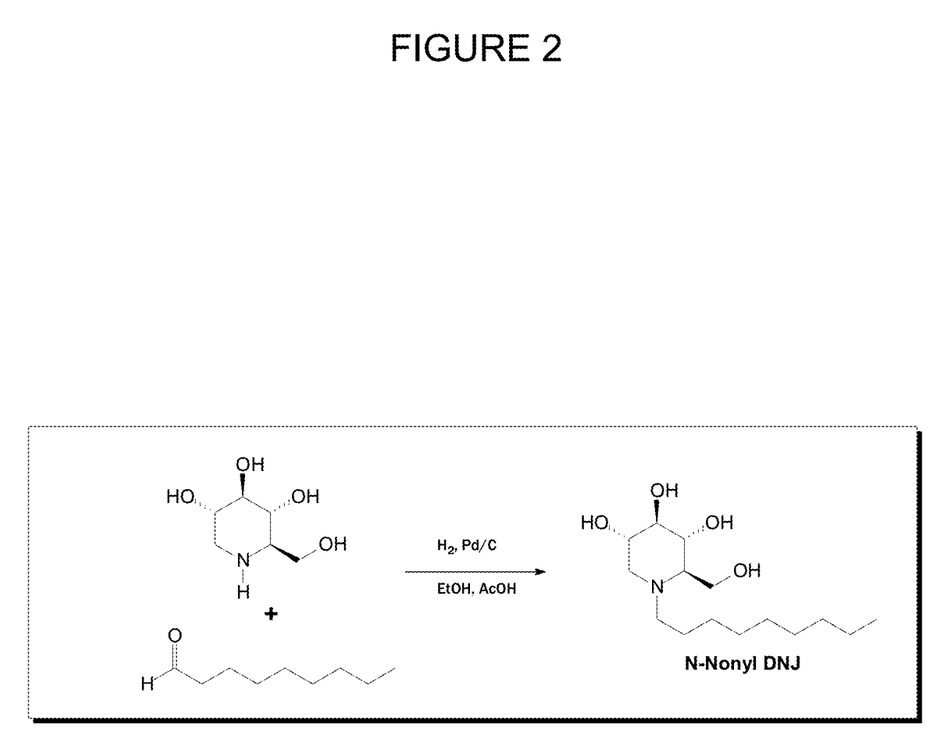
FIG. 2 is a synthesis scheme for NN-DNJ.
Figure 3A:
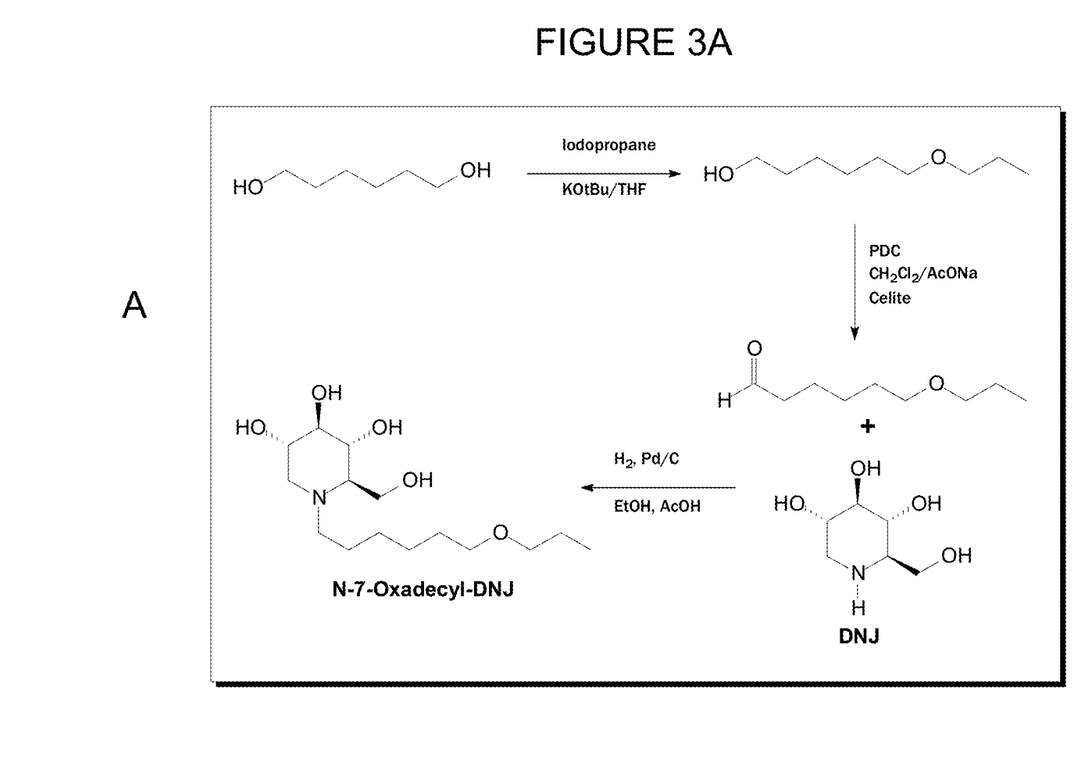
FIG. 3A shows a sequence of reactions leading to N7-O-DNJ.
Figure 3B:
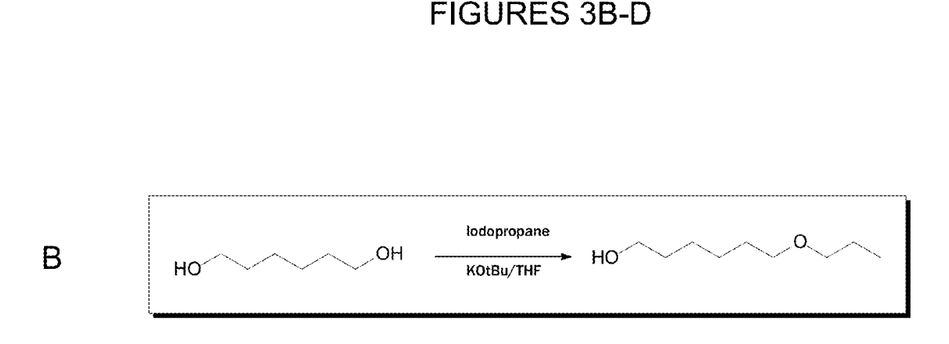
FIG. 3B illustrates preparation of 6-propyloxy-1-hexanol.
Figure 4A:
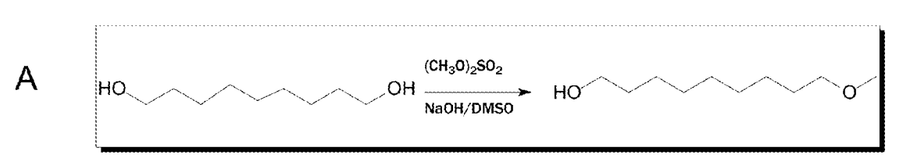
FIG. 4A illustrates preparation of 9-methoxy-1-nonanol.
Figure 4B:
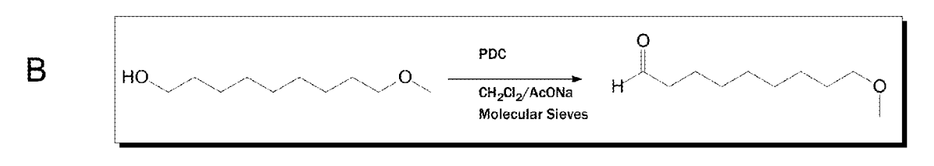
FIG. 4B illustrates preparation of 9-methoxy-1-nonanal.
Figure 4C:
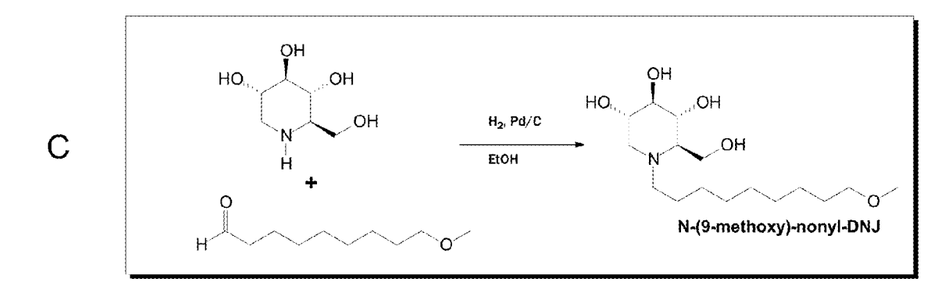

In some embodiments, the deoxynojirimycin derivative can be one of the compounds presented in FIG. 1.

Methods of synthesizing deoxynojirimycin derivatives are disclosed, for example, in U.S. Pat. Nos. 5,622,972, 5,200,523, 5,043,273, 4,994,572, 4,246,345, 4,266,025, 4,405,714, and 4,806,650 and U.S. Patent application publication no. 2007/0275998, which are all incorporated herein by reference.

In some embodiments, the iminosugar can be in a form of a salt derived from an inorganic or organic acid. Pharmaceutically acceptable salts and methods for preparing salt forms are disclosed, for example, in Berge et al. (*J. Pharm. Sci.* 66:1-18, 1977). Examples of appropriate salts include but are not limited to the following salts: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

In some embodiments, the iminosugar may also used in a form of a prodrug. Prodrugs of DNJ derivatives, such as the 6-phosphorylated DNJ derivatives, are disclosed in U.S. Pat. Nos. 5,043,273 and 5,103,008.

In some embodiments, the iminosugar may be used as a part of a composition, which further comprises a pharmaceutically acceptable carrier and/or a component useful for delivering the composition to an animal. Numerous pharmaceutically acceptable carriers useful for delivering the compositions to a human and components useful for delivering the composition to other animals such as cattle are known in the art. Addition of such carriers and components to the composition of the invention is well within the level of ordinary skill in the art.

In some embodiments, the iminosugar may be used in a liposome composition, such as those disclosed in US publication 2008/0138351; U.S. application Ser. No. 12/410,750 filed Mar. 25, 2009 and U.S. provisional application No. 61/202,699 filed Mar. 27, 2009.

The iminosugar, such as a DNJ derivative, can be administered to a cell or an animal affected by a virus. The iminosugar can inhibit morphogenesis of the virus, or it can treat the animal. The treatment can reduce, abate, or diminish the virus infection in the animal.

Animals that can be infected with a virus that belongs to the Bunyaviridae or Togaviridae family, include vertebrates, such as birds and mammals including primates, humans, rodents, livestock animals, such as sheep and goats, and equines such as horses, zebras and donkeys, as well as invertebrates.

The amount of iminosugar administered to a cell, or an animal can be an amount effective to inhibit the morphogenesis of a virus, that belongs to the Bunyaviridae or Togaviridae family. The term "inhibit" as used herein can refer to the detectable reduction and/or elimination of a biological activity exhibited in the absence of the iminosugar. The term "effective amount" can refer to that amount of the iminosugar necessary to achieve the indicated effect. The term "treatment" as used herein can refer to reducing or alleviating symptoms in a subject, preventing symptoms from worsening or progressing, inhibition or elimination of the causative agent, or prevention of the infection or disorder related to the virus that belongs to the Bunyaviridae or Togaviridae family in a subject who is free therefrom.

Thus, for example, treatment of the disease caused by or associated with a virus can include destruction of the infecting agent, inhibition of or interference with its growth or maturation, and neutralization of its pathological effects. The amount of the iminosugar which can be administered to the cell or animal is preferably an amount that does not induce any toxic effects which outweigh the advantages which accompany its administration.

Actual dosage levels of active ingredients in the pharmaceutical compositions may vary so as to administer an amount of the active compound(s) that is effective to achieve the desired therapeutic response for a particular patient.

The selected dose level can depend on the activity of the iminosugar, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient can depend on a variety of factors, including the body weight, general health, diet, time and route of administration and combination with other therapeutic agents and the severity of the condition or disease being treated. The adult human daily dosage may range from between about one microgram to about one gram, or from between about 10 mg and 100 mg, of the iminosugar per 10 kilogram body weight. Of course, the amount of the iminosugar which should be administered to a cell or animal can depend upon numerous factors well understood by one of skill in the art, such as the molecular weight of the iminosugar and the route of administration.

Pharmaceutical compositions that are useful in the methods of the invention may be administered systemically in oral solid formulations, ophthalmic, suppository, aerosol, topical or other similar formulations. For example, it may be in the physical form of a powder, tablet, capsule, lozenge, gel, solution, suspension, syrup, or the like. In addition to the iminosugar, such pharmaceutical compositions may contain pharmaceutically-acceptable carriers and other ingredients known to enhance and facilitate drug administration. Other possible formulations, such as nanoparticles, liposomes resealed erythrocytes, and immunologically based systems may also be used to administer the iminosugar. Such pharmaceutical compositions may be administered by a number of routes. The term "parenteral" used herein includes subcutaneous, intravenous, intraarterial, intrathecal, and injection and infusion techniques, without limitation. By way of example, the pharmaceutical compositions may be administered orally, topically, parenterally, systemically, or by a pulmonary route.

These compositions may be administered in a single dose or in multiple doses which are administered at different times. Because the inhibitory effect of the composition upon a virus, that belongs to the Bunyaviridae or Togaviridae family, may persist, the dosing regimen may be adjusted such that virus propagation is retarded while the host cell is minimally effected. By way of example, an animal may be administered a dose of the composition of the invention once per week, whereby virus propagation is retarded for the entire week, while host cell functions are inhibited only for a short period once per week.

Embodiments described herein are further illustrated by, though in no way limited to, the following working examples.

WORKING EXAMPLES

1. Synthesis of N-Nonyl DNJ

TABLE 1

Materials for NN-DNJ synthesis

| Name | Amount |
|---|---|
| DNJ | 500 mg |
| Nonanal | 530 mg |
| Ethanol | 100 mL |
| AcOH | 0.5 mL |
| Pd/C | 500 mg |

Procedure: A 50-mL, one-necked, round-bottom flask equipped with a magnetic stirrer was charged with DNJ (500 mg), ethanol (100 mL), nonanal (530 mg), and acetic acid (0.5 mL) at room temperature. The reaction mixture was heated to 40-45° C. and stirred for 30-40 minutes under nitrogen. The reaction mixture was cooled to ambient temperature and and Pd/C was added. The reaction flask was evacuated and replaced by hydrogen gas in a balloon. This process was repeated three times. Finally, the reaction mixture was stirred at ambient temperature overnight. The progress of reaction was monitored by TLC (Note 1). The reaction mixture was filtered through a pad of Celite and washed with ethanol. The filtrate was concentrated in vacuo to get the crude product. The crude product was purified by column chromatography (230-400 mesh silica gel). A solvent gradient of methanol in dichloromethane (10-25%) was used to elute the product from the column. All fractions containing the desired product were combined, and concentrated in vacuo to give the pure product (420 mg). Completion of the reaction was monitored by thin layer chromatography (TLC) using a thin layer silica gel plate; eluent; methanol:dichloromethane=1:2

2. Synthesis of N-7-Oxadecyl DNJ

2a. Synthesis of 6-propyloxy-1-hexanol

TABLE 2

Materials for synthesis of 6-propyloxy-1-hexanol

| Name | Amount |
|---|---|
| 1,6-hexanediol | 6.00 g |
| 1-Iodopropane | 8.63 g |
| Potassium tert-butoxide | 5.413 mg |
| THF | 140 mL |

Procedure: a 500-mL, one-necked, round-bottom flask equipped with a magnetic stirrer was charged with 1,6-hexanediol (6.00 g), potassium tert-butoxide (5.413 g) at room temperature. The reaction mixture was stirred for one hour, and then 1-iodopropane (8.63 g) was added. The reaction mixture was heated to 70-80° C. and stirred overnight. The progress of reaction was monitored by TLC (Note 1). After completion of the reaction, water was added to the reaction mixture, and extracted with ethyl acetate (2×100 mL). The combined organic layers were concentrated in vacuo to get the crude product. The crude product was dissolved in dichloromethane and washed with water, and then brine, dried over sodium sulfate. The organic layer was concentrated in vacuo to get the crude product. The crude product was purified by column chromatography using 230-400 mesh silica gel. A solvent gradient of ethyl acetate in hexanes (10-45%) was used to elute the product from the column. All fractions containing the desired pure product were combined and concentrated in vacuo to give pure 6-propyloxy-1-hexanol (lot D-1029-048, 1.9 g, 25%) Completion of the reaction was monitored by thin layer chromatography (TLC); (eluent: 60% ethyl acetate in hexanes).

2b. Preparation of 6-propyloxy-1-hexanal

TABLE 3

Materials for preparation of 6-propyloxy-1-hexanal

| Name | Amount |
|---|---|
| 6-Propyloxy-1-hexanol | 1.00 g |
| PDC | 4.70 g |
| Celite | 1.00 g |
| NaOAc | 100 mg |
| $CH_2Cl_2$ | 10 mL |

Procedure: a 50-mL, one-necked, round-bottom flask equipped with a magnetic stirrer was charged with 6-propyloxy-1-hexanol (1.0 g), PDC (4.7 g), dichloromethane (10 mL), Celite (1.0 g), and sodium acetate (100 mg). The reaction mixture was stirred at room temperature under nitrogen for 5 minutes. PDC (4.70 g) was added to the reaction mixture, and stirred overnight. The progress of reaction was monitored by TLC (Note 1). After completion of the reaction, the reaction mixture was directly loaded on the column (230-400 mesh silica gel). A solvent gradient of dichloromethane in ethyl acetate (10-20%) was used to elute the product from the column. All fractions containing the desired pure product were combined and concentrated in vacuo to give pure 6-propyloxy-1-hexanal (lot D-1029-050, 710 mg, 71%). Completion of the reaction was monitored by thin layer chromatography (TLC); (eluent: 60% ethyl acetate in hexanes).

2c Synthesis of N-7-Oxadecyl-DNJ

TABLE 4

Materials for Synthesis of N-7-Oxadecyl-DNJ

| Name | Amount |
| --- | --- |
| DNJ | 500 mg |
| 6-Propyloxy-1-hexanal | 585 mg |
| Pd/C | 125 mg |
| Ethanol | 15 mL |
| Acetic acid | mL |

Procedure: a 50-mL, one-necked, round-bottom flask equipped with a magnetic stirrer was charged with DNJ (500 mg), ethanol (15 mL), 6-propyloxy-1-hexanal (585 mg), and acetic acid (0.1 mL) t room temperature. The reaction mixture was heated to 40-45° C. and stirred for 30-40 minutes under nitrogen. The reaction mixture was cooled to ambient temperature and and Pd/C was added. The reaction flask was evacuated and replaced by hydrogen gas in a balloon. This process was repeated three times. Finally, the reaction mixture was stirred at ambient temperature overnight. The progress of reaction was monitored by TLC (Note 1). The reaction mixture was filtered through a pad of Celite and washed with ethanol. The filtrate was concentrated in vacuo to get the crude product. The crude product was purified by column chromatography (230-400 mesh silica gel). A solvent gradient of methanol in dichloromethane (10-40%) was used to elute the product from the column. All fractions containing the desired product were combined, and concentrated in vacuo to give the pure product. (Lot: D-1029-052 (840 mg). Completion of the reaction was monitored by thin layer chromatography (TLC); (eluent: 50% methanol in dichloromethane).

3. Synthesis of N-(9-methoxy)-nonyl DNJ

3a Preparation of 9-methoxy-1-nonanol

TABLE 5

Materials for preparation of 9-methoxy-1-nonanol

| Name | Amount |
| --- | --- |
| 1,9-nonanediol | 10.0 g |
| Dimethyl sulfate | 41.39 g |
| Sodium hydroxide | 5.0 g |
| DMSO | 100 mL |

Procedure: a 500-mL, one-necked, round-bottom flask equipped with a magnetic stirrer and stir bar was charged with 1,9-nonanediol (10.00 g, 62.3 mmol) in dimethyl sulfoxide (100 mL) and $H_2O$ (100 mL). To this was added slowly a solution of sodium hydroxide (5.0 g, 125.0 mmol) in $H_2O$ (10 mL) at room temperature. During addition of sodium hydroxide the reaction mixture generated heat and the temperature rose to ~40° C. The mixture was stirred for one hour, and then dimethyl sulfate (16.52 g, 131 mmol) was added in four portions while maintaining the temperature of the reaction mixture at ~40° C. The reaction mixture was stirred at room temperature overnight. Progress of the reaction was monitored by TLC (Note 1). TLC monitoring indicated that the reaction was 25% conversion. At this stage additional dimethyl sulfate (24.78 g, 196.44 mmol) was added and the resulting mixture was stirred at room temperature for an additional 24 h. After completion of the reaction, sodium hydroxide (10% solution in water) was added to the reaction mixture to adjust the pH of the solution to 11-13. The mixture was stirred at room temperature for 2 h and extracted with dichloromethane (3×100 mL). The combined organic layers were washed with $H_2O$ (200 mL), brine (150 mL), dried over anhydrous sodium sulfate (20 g), filtered and concentrated in vacuo to obtain a crude product (14 g). The crude product was purified by column chromatography using 250-400 mesh silica gel. A solvent gradient of ethyl acetate in hexanes (10-50%) was used to elute the product from the column. All fractions containing the desired pure product were combined and concentrated in vacuo to give pure 9-methoxy-1-nonanol (lot D-1027-155, 2.38 g, 21.9%). Completion of the reaction was monitored by thin layer chromatography (TLC) using a thin layer silica gel plate; eluent: 60% ethyl acetate in hexanes.

3b Preparation of 9-methoxy-1-nonanal

TABLE 6

Materials for preparation of 9-methoxy-1-nonanal

| Name | Amount |
| --- | --- |
| 9-methoxy-1-nonanol | 1.0 g |
| PDC | 4.7 g |
| Molecular sieves, 3A | 1.0 g |
| NaOAc | 0.1 g |
| $CH_2Cl_2$ | 10 mL |

Procedure: a 50-mL, one-necked, round-bottom flask equipped with a magnetic stirrer and stir bar was charged with 9-methoxy-nonanol (1.0 g, 5.9 mmol), dichloromethane (10 mL), molecular sieves (1.0 g, 3 A), sodium acetate (0.1 g) at room temperature. The reaction mixture was stirred at room temperature under nitrogen for 5 minutes. The reaction mixture was charged with pyridinium dichromate (4.7 g, 12.5 mmol) and stirred overnight. The progress of reaction was monitored by TLC (Note 1). After completion of the reaction, the reaction mixture was filtered through a bed of silica gel (~15 g). The filtrate was evaporated in vacuo to obtain a crude compound. This was purified by column chromatography using silica gel column (250-400 mesh, 40 g). A solvent gradient of ethyl acetate in hexane (10-50%) was used to elute the product from the column. All fractions containing the desired pure product were combined and concentrated in vacuo to give pure 9-methoxy-nonanal (lot D-1027-156, 553 mg, 54.4%). Completion of the reaction was monitored by thin layer chromatography (TLC) using a thin layer silica gel plate; eluent: 60% ethyl acetate in hexanes.

3c Synthesis of N-(9-methoxy)-nonyl DNJ

TABLE 7

Materials for synthesis of N-(9-methoxy)-nonyl DNJ

| Name | Amount |
| --- | --- |
| DNJ | 300 mg |
| 9-methoxy-1-nonanal | 476 mg |

TABLE 7-continued

Materials for synthesis of N-(9-methoxy)-nonyl DNJ

| Name | Amount |
|---|---|
| Pd/C | 200 mg |
| Ethanol | 20 mL |

Procedure: a 50-mL, two-necked, round-bottom flask equipped with magnetic stirrer and a stir bar was charged with DNJ (300 mg, 1.84 mmol), ethanol (20 mL), 9-methoxy-1-nonanal (476 mg, 2.76 mmol) at room temperature. The reaction mixture was stirred for 5-10 minutes under nitrogen and Pd/C was added at room temperature. The reaction mixture was evacuated and was replaced by hydrogen gas using a balloon. This process was repeated three times and then reaction mixture was stirred under atmospheric hydrogen at room temperature. The progress of reaction was monitored by TLC (Note 1). The reaction mixture was filtered through a bed of Celite and was washed with ethanol (20 mL). The filtrate was concentrated in vacuo to get a crude product. The crude product was purified by column chromatography using 250-400 mesh silica gel (20 g). A solvent gradient of methanol in ethyl acetate (5-25%) was used to elute the product from the column. All fractions containing the desired pure product were combined, and concentrated in vacuo to give an off white solid. The solid was triturated in ethyl acetate (20 mL), filtered and dried in high vacuum to give a white solid [lot: D-1027-158 (165.3 mg, 28.1%). Completion of the reaction was monitored by thin layer chromatography (TLC) using a thin layer silica gel plate; eluent: 50% methanol in dichloromethane.

4. Inhibition of Selected Bunyaviruses and Togaviruses

Figure 5:
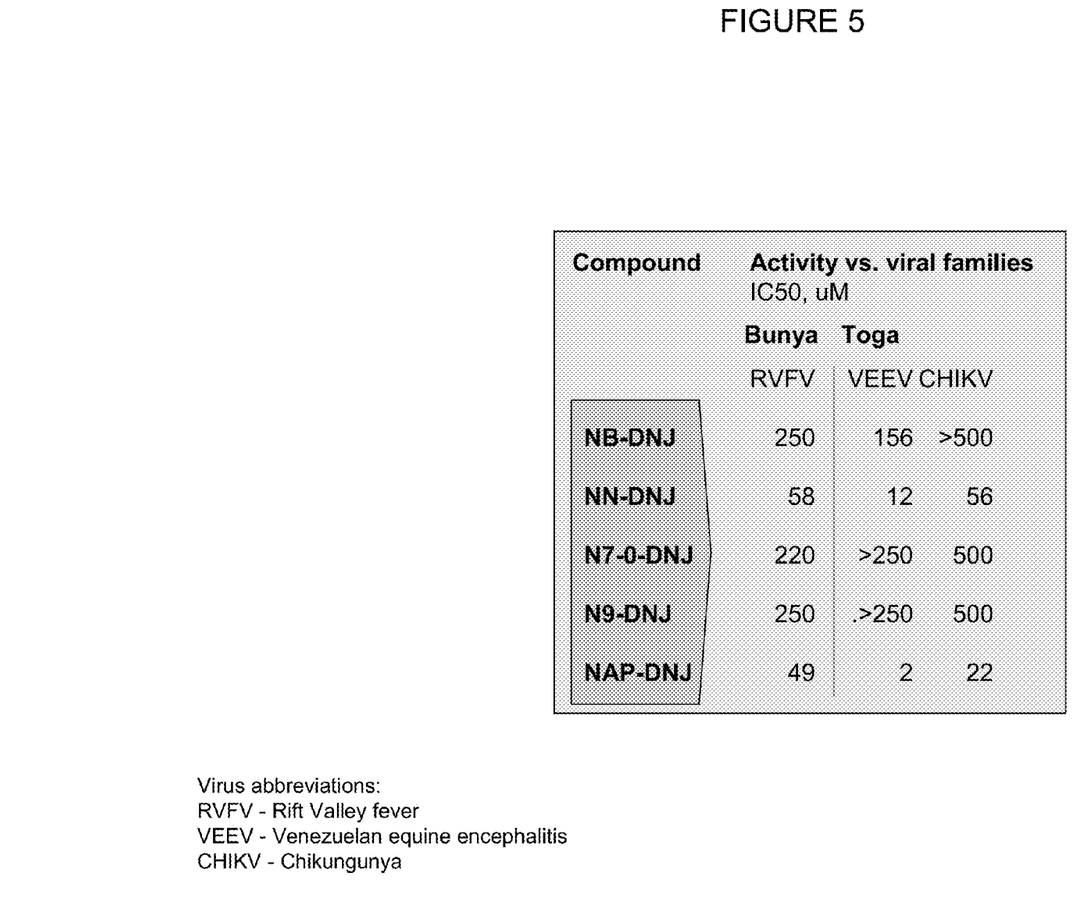
FIG. 5 presents a table with in vitro IC50 (μm) data for NB-DNJ; NN-DNJ; N7-O-DNJ; N9-DNJ and NAP-DNJ against selected Bunyaviruses (Rift Valley Fever virus (RVFV)) and Togaviruses (Venezuelan equine encephalitis virus (VEEV)) and Chikingunya virus (CHIKV)).

FIG. 5 presents a table with in vitro IC50 (μm) data for NB-DNJ; NN-DNJ; N7-O-DNJ; N9-DNJ and NAP-DNJ against Rift Valley Fever virus (RVFV)), which is a Bunyavirus, and Venezuelan equine encephalitis virus (VEEV)) and Chikingunya virus (CHIKV), which are Togaviruses.

Compounds. Base stocks of the following compounds were prepared in dimethylsulfoxide (DMSO) to a final maximal DMSO concentration of 0.5%: NB-DNJ, NN-DNJ, N7-O-DNJ, N9-DNJ, and NAP-DNJ. All compounds were diluted from the base stocks to their experimental concentrations.

Viruses. The compounds were screened for inhibition against Rift Valley Fever Virus (Bunyavirus) MP12 strain, Chikungunya (Togaviridae) 181/25 strain, and the Venezuelan Equine Encephalitis (Togaviridae) TC-83 strain. Viral stocks were made by propagation in Vero cells using modified Eagle medium (MEM, Sigma), supplemented with 2% fetal bovine serum, 2 mM L-glutamine, 100 U/ml penicillin, 100 ug/ml streptomycin and titered using the standard plaque assay (method presented below). Viral stocks were stored at −80° C. until used.

Virus Yield Reduction Assay. The virus yield assay were performed by standard plaque assay on supernatant samples generated from virus-infected cells incubated with different concentrations of the UV compound. 24-well cell culture plates were seeded with cells in 1 mL MEM with 10% fetal bovine serum Vero cells (ATCC, Mannassas, Va.; ATCC number CCL-81) in MEM with Earl's salts (Sigma, St Louis, Mo.) supplemented with 2 mM L-glutamine, 100 U/mL penicillin/streptomycin, and 2% heat-inactivated fetal bovine serum and incubated at 37° C. for 24 hours or until ~80% confluency. Medium were replaced with medium supplemented with 2% fetal bovine serum and the compound concentrations to be used started at 250 uM (or 125 uM) and tested in triplicate using 8 dilutions. compounds starting at 250 or 125 uM dilution is added to appropriate well and incubated for 1 hr at 37° C., 5% $CO_2$. After 1 hr incubation virus is added to each well. Four days are required for the RVFV, three days for CHIKV, and two days for VEE virus infection. Upon completion of infection, supernatant were harvested and collected in 0.5 mL MCF tubes for titering.

To titer RVFV MP12, CHIKV 181/25, and VEE TC-83, 12-well plates with 80% confluent Vero cells in growth medium were used. Viral supernatant were diluted from $10^{-3}$ to $10^{-8}$ and added (100 uL) to the cells and incubated at 37° C. for 1 hour with shaking every 5-10 minutes. Viral infection medium (100 uL) were aspirated and replace with 1 mL pre-warmed 2% low-melt agarose mixed 1:1 with 2× MEM (5% fetal calf serum) and incubated at 37° C., 5% $CO_2$ for 6 days followed by plaque visualization by neutral red staining IC50 was determined as concentration of compound resulting in 50% virus inhibition.

Figure 6:
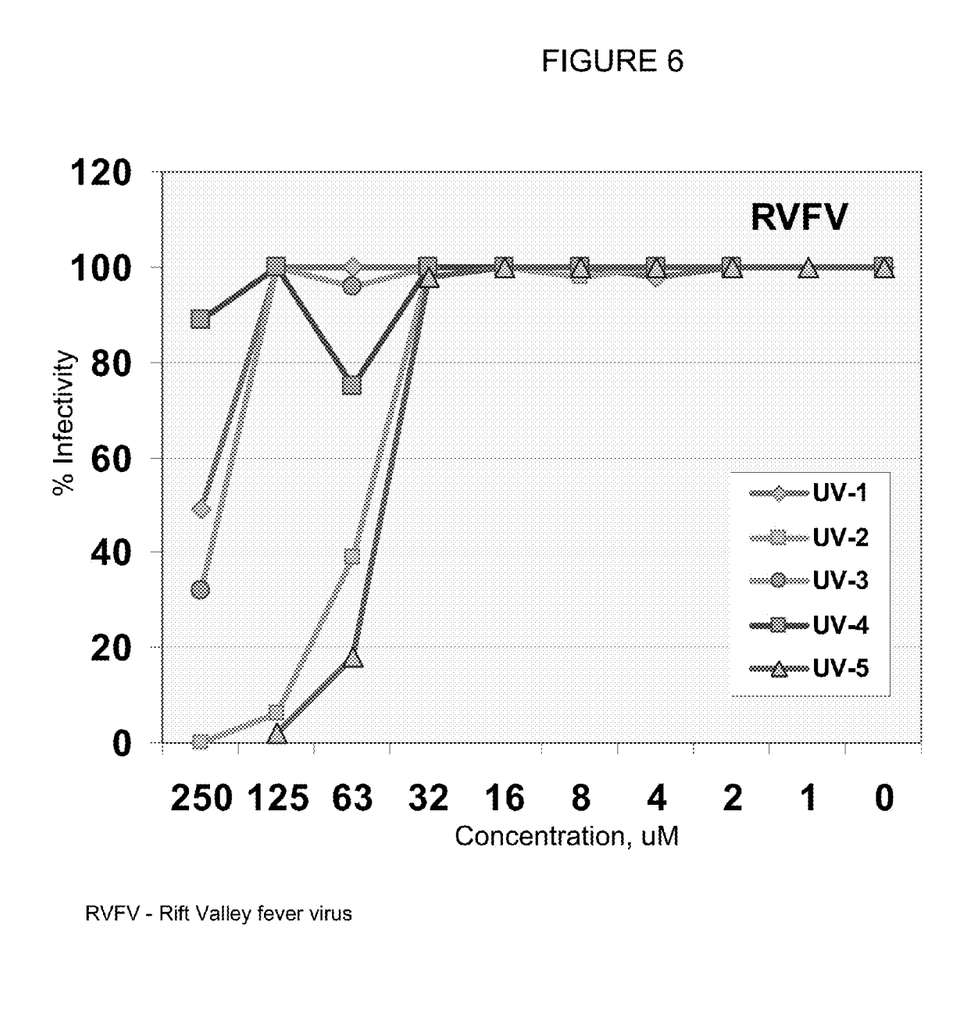
FIG. 6 presents dose response curves for Rift Valley Fever virus (RVFV).

FIG. 6 presents dose response curves for Rift Valley Fever virus (RVFV). The virus yield assay were performed as disclosed for FIG. 5. RVFV MP12 virus inhibition was found for compounds UV-2 (NN-DNJ), -3 (N7-O-DNJ), and -5 (NAP-DNJ) with EC50s of 58, 218, and 49 μM. UV-2 was toxic to cells at the highest concentration (250 μM). Compounds UV-1 (NB-DNJ) and -4 (N9-DNJ) all have EC50s over 250 μM.

Figure 7:
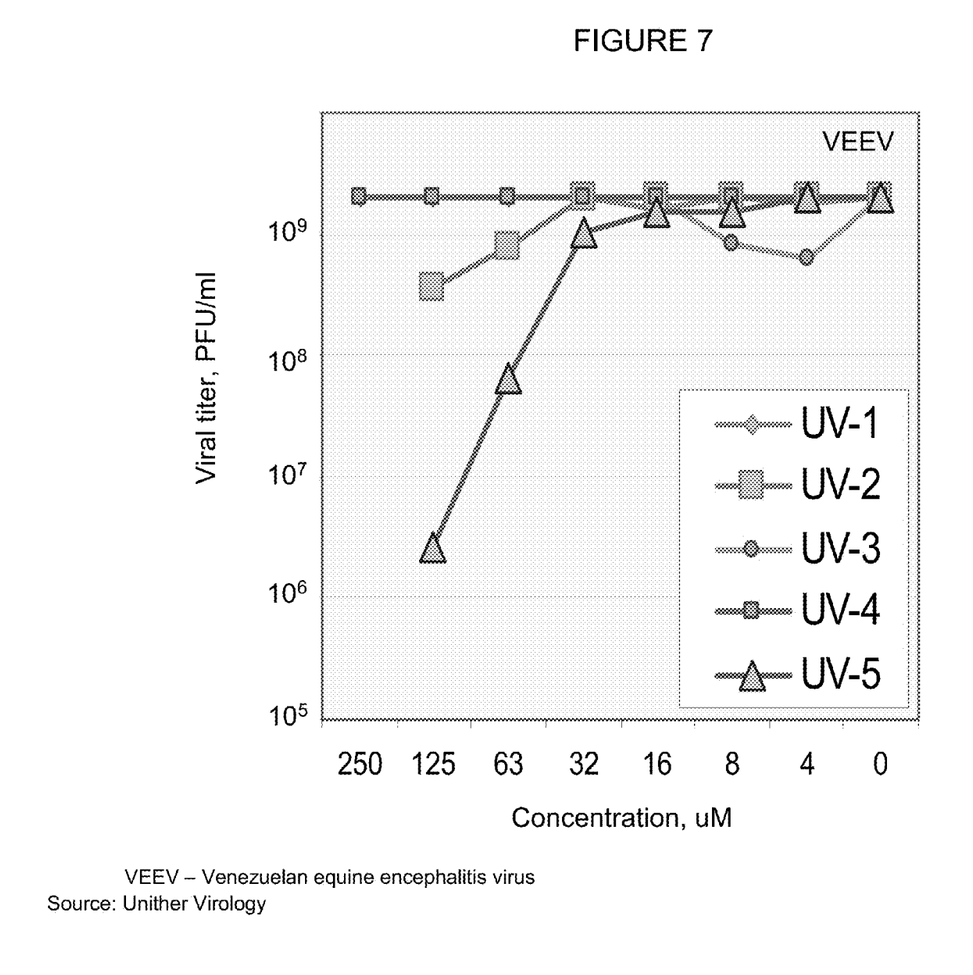
FIG. 7 presents dose response curves for Venezuelan equine encephalitis virus (VEEV).

FIG. 7 presents dose response curves for Venezuelan equine encephalitis virus (VEEV). The virus yield assay were performed as disclosed above for FIG. 5. VEE virus inhibition was found for compounds UV-1 (NB-DNJ), -2 (NN-DNJ), and -5 (NAP-DNJ) with EC50s of 156, 12, and 2 μM. UV-2 was toxic at the highest concentration (250 μM). Compounds UV-3 (N7-O-DNJ) and -4 (N9-DNJ) all had EC50s over 250 μM.

Figure 8:
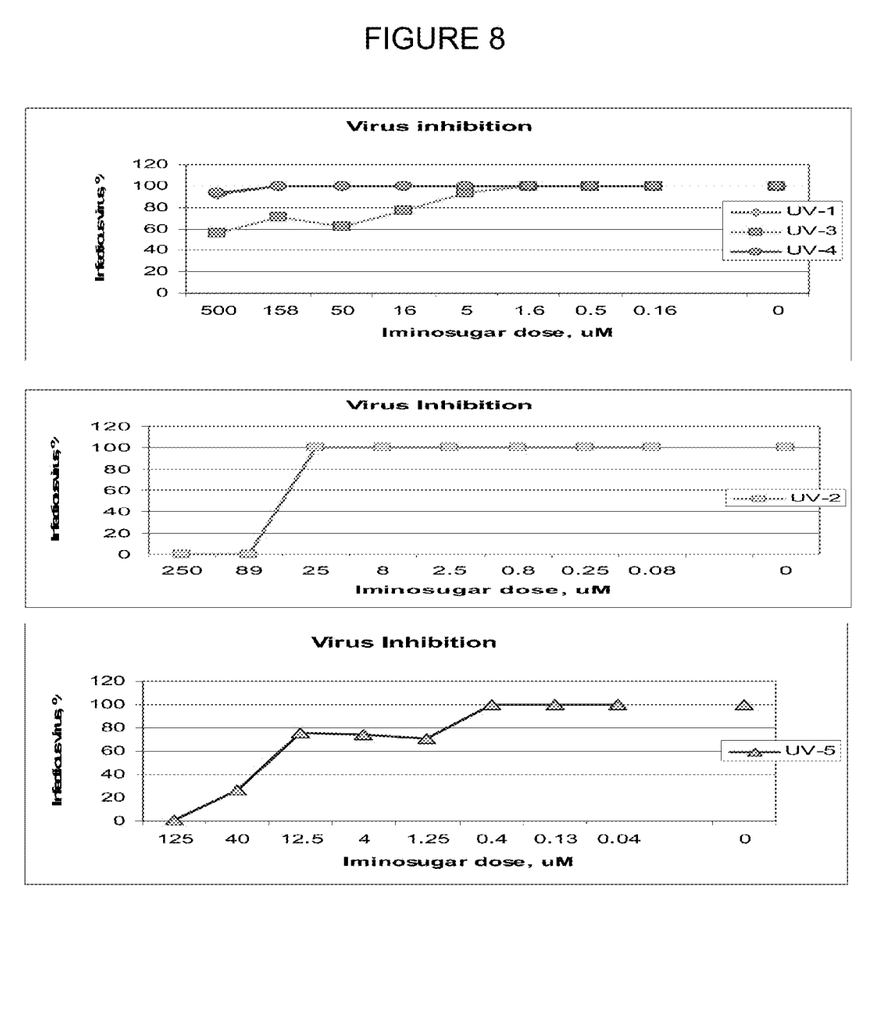
FIG. 8 presents dose response curves for Chikingunya virus (CHIKV).

FIG. 8 presents dose response curves for Chikingunya virus (CHIKV). The virus yield assay were performed as in FIG. 5. Chikungunya virus inhibition was found for compounds UV-5 (NAP-DNJ) with an EC50 of 22 μM. UV-2 (NN-DNJ) showed protection with an EC50 of 56 μM. Compounds UV-1 (NB-DNJ), -3 (N7-O-DNJ), -4 (N9-DNJ) all have EC50s over 500 μM.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of treating a disease or condition caused by or associated with a virus belonging to the Togaviridae family, the method comprising administering to a subject in need thereof a compound of the formula, or a pharmaceutically acceptable salt thereof, wherein R is either selected from substituted or unsubstituted alkyl groups, substituted or unsubstituted cycloalkyl groups, substituted or unsubstituted aryl groups, or substituted or unsubstituted oxaalkyl groups; or wherein R is

$R_1$ is a substituted or unsubstituted alkyl group;
$X_{1-5}$ are independently selected from H, $NO_2$, $N_3$, or $NH_2$;
Y is absent or is a substituted or unsubstituted $C_1$-alkyl group, other than carbonyl; and
Z is selected from a bond or NH; provided that when Z is a bond, Y is absent, and provided that when Z is NH, Y is a substituted or unsubstituted $C_1$-alkyl group, other than carbonyl; and wherein $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups.

2. The method of claim 1, wherein R is a C8-C16 alkyl group.

3. The method of claim 2, wherein each of $W_{1-4}$ is hydrogen.

4. The method of claim 3, wherein the compound is N-nonyl-deoxynojirimycin or a pharmaceutically acceptable salt thereof.

5. The method of claim 1, wherein R is

6. The method of claim 5, wherein each of $W_{1-4}$ is hydrogen.

7. The method of claim 5, wherein $X_1$ is $NO_2$ and $X_3$ is $N_3$.

8. The method of claim 5, wherein each of $X_2$, $X_4$ and $X_5$ is hydrogen.

9. The method of claim 5, wherein the compound is N—(N-{4'-azido-2'-nitrophenyl}-6-aminohexyl)deoxynojirimycin or a pharmaceutically acceptable salt thereof.

10. The method of claim 1, wherein the subject is a mammal.

11. The method of claim 1, wherein the subject is a human being.

12. The method of claim 1, wherein the virus is selected from Sindbis virus; Semliki Forest virus; O'nyong'nyong virus; Chikungunya virus; Mayaro virus; Ross River virus; Barmah Forest virus; Eastern equine encephalitis virus; Western equine encephalitis virus; Venezuelan equine encephalitis virus and Rubella virus.

13. The method of claim 1, wherein the virus belongs to Genus *Alphavirus*.

14. The method of claim 1, wherein the virus is Chikungunya virus.

15. The method of claim 1, wherein the virus is Venezuelan equine encephalitis virus.

16. The method of claim 1, wherein the disease or condition is selected from sindbis fever; O'nyong'nyong fever; Chikungunya disease; Ross River fever; Barmah Forest virus infection; Eastern equine encephalitis; Western equine encephalitis; Venezuelan equine encephalitis and Rubella.

17. The method of claim 1, wherein the disease or condition is Chikungunya disease.

18. The method of claim 1, wherein the disease or condition is equine encephalitis.

19. The method of claim 1, wherein the disease or condition is Venezuelan equine encephalitis.

* * * * *